United States Patent [19]

Goto et al.

[11] Patent Number: 5,047,430

[45] Date of Patent: Sep. 10, 1991

[54] AMIDE COMPOUNDS, THEIR PRODUCTION AND USE

[75] Inventors: Giichi Goto, Osaka; Terumi Nakajima, Tokyo, both of Japan

[73] Assignee: Takeda Chemical Industries, Ltd., Osaka, Japan

[21] Appl. No.: 342,965

[22] Filed: Apr. 25, 1989

[30] Foreign Application Priority Data

Apr. 26, 1988 [JP] Japan ............................... 63-105080

[51] Int. Cl.$^5$ ..................... A01N 37/18; A61K 31/16
[52] U.S. Cl. ................................ 514/616; 564/153; 546/316; 549/487; 514/316; 514/355
[58] Field of Search ........................ 564/153; 514/616

[56] References Cited

U.S. PATENT DOCUMENTS 4,918,107 4/1990 Nakajima et al. ................... 514/616

FOREIGN PATENT DOCUMENTS 63-190964 8/1988 Japan ................................... 564/153
63-218603 9/1988 Japan.
63-310856 12/1988 Japan ................................... 564/153

OTHER PUBLICATIONS

Teshima et al., *Tetrahedron Letters*, vol. 28, No. 30, pp. 3509-3510, 1987.
Hashimoto et al., *Peptide Chemistry*, vol. Date 1987, pp. 363-366.
Aramaki et al., *Peptide Chemistry*, vol. Date 1987, pp. 163-166.
*Proceedings of the Japan Academy*, 62, Ser. B, pp. 359-362.
Aramaki et al., *Biomedical Research*, 8(4), pp. 241-245, 1987.

*Primary Examiner*—Glennon H. Hollrah
*Assistant Examiner*—Scott L. Rand
*Attorney, Agent, or Firm*—Wegner, Cantor, Mueller & Player

[57] ABSTRACT

A compound is provided which has the formula

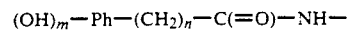
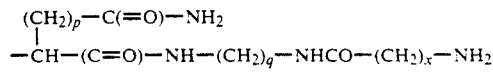

wherein
m is an integer of 1 to 3;
n is an integer of 1 or 2;
p is an integer of 1 or 2;
q is an integer of 1 to 6;
x is an integer of 2 to 6;
Ph is phenylene or a pharmceutically acceptable salt thereof. Also provided is a method for glutamate receptor inhibition which comprises administering to a mammal in need thereof an effective amount of said compound or a pharmaceutically acceptable salt thereof. Compositions for glutamate receptor inhibition are provided which contain an effective amount of said compound to provide a glutamate receptor inhibition effect, together with at least one pharmaceutically acceptable carrier, dilient or excipient therefor.

7 Claims, No Drawings

AMIDE COMPOUNDS, THEIR PRODUCTION AND USE

SUMMARY OF THE INVENTION

In a first aspect of the invention there is provided a compound of the formula $$(OH)_m-Ph-(CH_2)_n-C(=O)-NH-$$

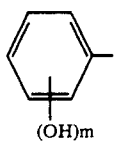

$$\begin{array}{c}(CH_2)_p-C(=O)-NH_2\\|\\-CH-(C=O)-NH-(CH_2)_q-NHCO-(CH_2)_x-NH_2\end{array}$$

wherein
m is an integer of 1 to 3;
n is an integer of 1 or 2;
q is an integer of 1 to 6;
x is an integer of 2 to 6;
Ph is phenylene
or a pharmaceutically acceptable salt thereof.

In accordance with a second aspect of the invention, there is provided a method for glutamate receptor inhibition which comprises administering to a mammal in need thereof an effective amount of said compound or a pharmaceutically acceptable salt thereof.

In accordance with a third aspect of the invention, there is provided a composition for glutamate receptor inhibition which contains an effective amount of said compound to provide a glutamate receptor inhibition effect, together with at least one pharmaceutically acceptable carrier, dilient or excipient therefor.

DETAILED DESCRIPTION OF THE INVENTION

The presence of chemical substances in spiders which paralyze the nerve of anthropodes such as insects has been elucidated and such substances have been isolated. It has also been confirmed that the nerve paralyzing action of those substances is due to glutamic receptor inhibiting action [N. Kawai, A. Miwa, T. Abe, Brain Res., 247 169-171 (1982); N. Kawai, A. Miwa, M. Saito, M. Yoshioka, Microelectrophoretic Investigations of Mammalian Central Transmitters, Aug. 25, 1983, Camberra, Australia, Lecture Summaries p. 4; N. Kawai, A. Miwa, M. Saito, M. Yoshioka, 29th Congress of the International Union of Physiological Sciences, Aug. 29, 1983, Sydney, Australia, Lecture Summaries p. 89; N. Kawai, 8th Conference en Neurobiologie, Nov. 25, 1983, Gif, France, Lecture Summaries, P. 10; N. Kawai, A. Miwa, T. Abe, Advances in Biological Psychopharmacology, 37 221-227 (1983); T. Abe, N. Kawai, A. Miwa, J. Physiol., 339 243-252 (1983); N. Kawai, A. Miwa, T. Abe, Biomed. Res. 3 353-5 (1982); N. Kawai, S. Yamagishi, M. Saito, K. Furuya, Brain Res., 278 346-349 (1983); and U.S. patent application Ser. No. 59517]. Some of the relevant chemical structures have been reported. For instance, "Proceedings of the Japan Academy", 62 Ser. B, 359 (1986) discloses $N^1$-(2,4-dihydroxyphenylacetylasparaginyl)-$N^5$-(arginyl-cadaverino-$\beta$-alanyl)cadaverine and the like and Chemical Abstracts, 105: 186106d (1986) discloses (2,4-dihydroxyphenylacetylasparaginyl)-polyamine-(arginyl) wherein the polyamine a is $-NH(CH_2)_3NH(CH_2)_3NH(CH_2)_5NH-$. Nakajima et al., U.S. Pat. No. 4,918,107 (not prior art by virtue of the date of filing subsequent to the priority date of this application) discloses compounds which are cited to show the state of the art.

Contemplated are compounds of the general formula:

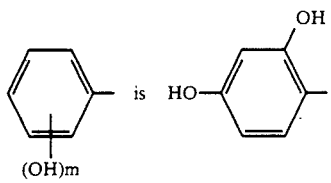

wherein R is a hydrogen atom or an acyl group, m is an integer of 1 to 3, n is an integer of 1 to 4, p is an integer of 1 to 2, q is an integer of 1 to 6, x is an integer of 2 to 6 and y is an integer of 1 to 3, with the proviso that, when (i)

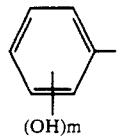

(ii) n is 1, (iii) p is 1, (iv) q is 5 and (v) R is a hydrogen atom, $[(CH_2)_x-NH]_y$ is neither $(CH_2)_2NH(CH_2)_3NH(CH_2)_3NH$ nor $(CH_2)_2NH(CH_2)_4NH(CH_2)_3NH$, or that, when

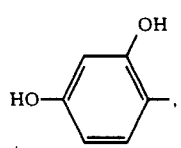

n is an integer of 2 to 4, p is 2 or $[(CH_2)_x-NH]_y-R$ is $(CH_2)_2NH_2$, or a salt thereof (referred to as "compound I" hereinafter).

The symbol R in compound I is a hydrogen atom or an acyl group. As the acyl group, mention may be made of, for example, a $C_{1-6}$ alkanoyl group (e.g., formyl, acetyl, propionyl, butyryl, isobutyryl, etc.), a $C_{2-6}$ alkenoyl group (e.g., acryloyl, crotonoyl, etc.), an aromatic carbonyl group such as $C_{6-10}$ arylcarbonyl (e.g., benzoyl, etc.), and a 5- or 6-membered nitrogen- or oxygen-containing heterocyclic carbonyl group (e.g., nicotinoyl, furanoyl, etc.). These acyl groups may be further substituted with for example one or two groups selected from halogen atom (fluorine, chlorine, bromine, iodine, etc.), hydroxyl group, thiol group, carboxyl group and carbamoyl group. Preferred examples of R include H.

The symbol m in compound I is an integer of 1 to 3. That is, 1 to 3 hydroxyl groups may be attached to any of the 2,3,4,5 and 6 positions of the benzene ring and examples thereof are 2-hydroxyphenyl, 3-hydroxyphenyl, 4-hydroxyphenyl, 2,4-dihydroxyphenyl, 2,5-dihydroxyphenyl, 3,4-dihydroxyphenyl and 2,4,5-trihydroxyphenyl. Preferred examples of m include 1 and 2. Accordingly preferred examples of

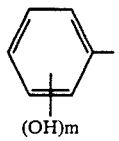

include groups of

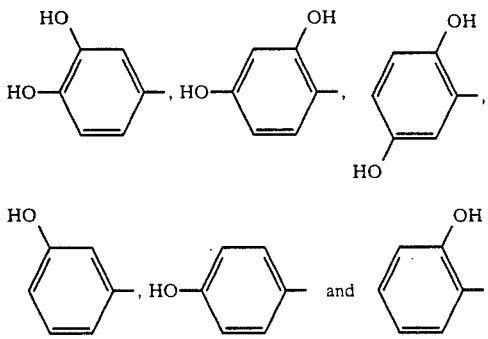

The symbol n in compound I is an integer of 1 to 4. That is, $-(CH_2)_n-$ indicates $-CH_2-$, $-(CH_2)_2-$, $-(CH_2)_3-$ or $-(CH_2)_4-$. Preferred examples of n include 1 and 2.

The symbol p in compound I is an integer of 1 to 2. That is,

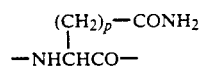

indicates

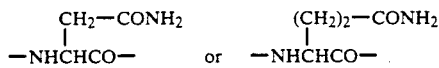

which may be abbreviated as —Asn— or —Gln— in this specification, respectively.

The symbol q in compound I is an integer of 1 to 6. That is, $-(CH_2)_q-$ indicates $-CH_2-$, $-(CH_2)_2-$, $-(CH_2)_3-$, $-(CH_2)_4-$, $-(CH_2)_5-$ or $-(CH_2)_6-$. Preferred examples of q include 5.

The symbols x and y of $-[(CH_2)_x-NH]_y-$ in compound I are an integer of 2 to 6 and an integer of 1 to 3, respectively. That is, $-[(CH_2)_x-NH]_y-$ indicates $-(CH_2)_{x_1}-NH-$ when y is 1, and $-(CH_2)_{x_2}-NH-(CH_2)_{x_3}-NH-$ when y is 2, and $-(CH_2)_{x_4}-NH-(CH_2)_{x_5}-NH-(CH_2)_{x_6}-NH-$ when y is 3, respectively, with the proviso that each of the symbols $x_1$ to $x_6$ is independently an integer of 2 to 6 like x. Preferred examples of $[(CH_2)_x-NH]_y$ include groups of $(CH_2)_2NH$ and $(CH_2)_2NH(CH_2)_4NH(CH_2)_3NH$.

Compound I may be a salt with an inorganic acid or organic acid. Examples of salts of inorganic acids are hydrochlorides, sulfates, carbonates and nitrates and examples of salts of organic acids are formates, acetates, propionates, oxalates, succinates, benzoates and p-toluenesulfonates. Preferred examples of the salts include hydrochlorides and acetates. Further, compound I may be a complex salt with a metal such as calcium, zinc, magnesium, cobalt, copper or iron. The amino acid which constitutes compound I may be of the L-form, D-form or DL-form, but the L-form is preferred.

Compound I may be produced, for example, by the following process.

Compound I may be produced by reacting a carboxylic acid [II] of the formula:

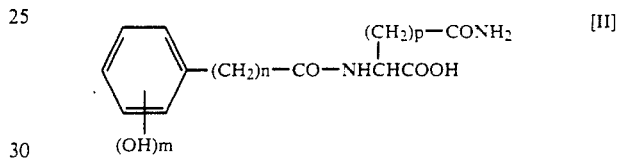

wherein the symbols are the same as defined above, or a salt or a reactive derivative thereof (referred to as "compound II" hereinafter) with a compound [III] of the formula:

$$NH_2(CH_2)_q-NHCO-[(CH_2)_x-NH]_y-R \qquad [III]$$

wherein the symbols are the same as defined above, or a salt thereof (referred to as "compound III" hereinafter) and, if necessary, eliminating a protecting group (Reaction formula 1).

Reaction formula 1

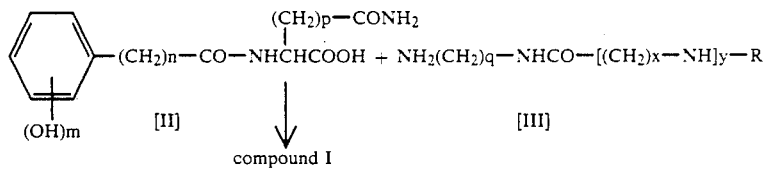

compound I

In the above reaction formula 1, the starting compound [II] may be a salt or a reactive derivative thereof and the starting compound [III] may be a salt.

The salt of compound [II] includes inorganic base salts or organic base salts of [II]. Examples of the inorganic base salts of [II] are alkali metal salts, e.g., a sodium salt or a potassium salt and alkaline earth metal salts, e.g., a calcium salt. Examples of the organic base salts of [II] are a trimethylamine salt, triethylamine salt, tert-butyldimethylamine salt, cyclohexylamine salt, dibenzylmethylamine salt, benzyldimethylamine salt, N,N-dimethylaniline salt, pyridine salt or quinoline salt. The reactive derivative of the starting compound [II] means a reactive derivative at the carboxyl group of the compound. The reactive derivative of compound [II] includes acid halides, acid azides, acid anhydrides, mixed acid anhydrides, active amides, active esters and active thioesters. Examples of acid halides of [II] are the acid chloride and the acid bromide. Examples of the mixed acid anhydrides are monoalkylcarbonic acid-mixed acid anhydrides, e.g., mixed acid anhydrides of [II] with monomethylcarbonic acid, monoethylcarbonic acid, monoisopropylcarbonic acid, monoisobutylcarbonic acid, mono-tert-butylcarbonic acid, monobenzylcarbonic acid, mono-(p-nitrobenzyl)carbonic acid or monoallylcarbonic acid, aliphatic carboxylic acid-mixed acid anhydrides, e.g., mixed acid anhydrides of [II] with acetic acid, trichloroacetic acid, cyanoacetic acid, propionic acid, butyric acid, isobutyric acid, valeric acid, isovaleric acid, pivalic acid, trifluoroacetic acid, trichloroacetic acid or acetoacetic acid, aromatic carboxylic acid-mixed acid anhydrides, e.g., mixed acid anhydrides of [II] with benzoic acid, p-toluic acid or p-chlorobenzoic acid and organic sulfonic acid-mixed acid anhydrides, e.g., mixed acid anhydrides of [II] with methanesulfonic acid, ethanesulfonic acid, benzenesulfonic acid or p-toluenesulfonic acid. Examples of the active amides are amides with nitrogen-containing heterocyclic compounds, e.g., acid amides of [II] with pyrazole, imidazole or benzotriazole and these nitrogen-containing heterocyclic compounds may have a substituent such as a $C_{1-4}$ alkyl group (e.g., methyl), a $C_{1-4}$ alkoxy group (e.g., methoxy), a halogen atom (e.g., Br,Cl,F), an oxo group, a thioxo group or a $C_{1-4}$ alkylthio group (e.g., methylthio). As active esters of [II], there may be used all of those which are used for the synthesis of peptides. Examples thereof include, in addition to organic phosphates, e.g., diethoxy phosphate and diphenoxy phosphate, p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester and 1-hydroxy-1H-2-pyridone ester. Examples of the active thioesters of [II] include esters with aromatic heterocyclic thiol compounds, e.g., 2-pyridylthiol ester and 2-benzothiazolyl-thiol ester and these heterocyclic rings may have a substituent such as an alkyl group, an alkoxy group, a halogen atom or an alkylthio group.

One to three hydroxyl groups on the benzene ring of the starting compound II may be protected with an easily removable protecting group. As examples of the protecting groups, mention may be made of substituted or unsubstituted alkanoyl groups, e.g., acetyl, propionyl and trifluoroacetyl, substituted oxycarbonyl groups, e.g., methoxycarbonyl, ethoxycarbonyl, isopropoxycarbonyl, tert-butoxycarbonyl, phenoxycarbonyl, benzyloxycarbonyl, p-methylbenzyloxycarbonyl or benzhydryloxycarbonyl, a tert-butyl group, aralkyl groups, e.g., benzyl, p-methylbenzyl, p-methoxybenzyl, p-chlorobenzyl, benzhydryl and trityl, and substituted silyl groups, e.g., trimethylsilyl and tert-butyldimethylsilyl. Preferred examples of the protecting group for the hydroxyl group include $C_{7-10}$ aralkyl such as benzyl and p-methylbenzyl.

The salt of the starting compound [III] includes salts with inorganic acids or organic acids. Examples of the inorganic acid salts include hydrochloride, hydrobromide, sulfate, nitrate and phosphate. Examples of the organic acid salts include formate, acetate, trifluoroacetate, methanesulfonate and p-toluenesulfonate.

The imino group (including the amino group in the case of R being a hydrogen atom) of the starting compound [III] may be protected with an easily removable protecting group. As examples of the protecting groups for the imino group, mention may be made of substituted or unsubstituted alkanoyl groups, e.g., formyl, acetyl, monochloroacetyl, trichloroacetyl, monoiodoacetyl, 3-oxobutyryl, p-chlorophenylacetyl and p-chlorophenoxyacetyl, aromatic carbonyl groups, e.g., benzoyl and p-tert-butylbenzoyl, substituted oxycarbonyl groups, e.g., methoxycarbonyl, ethoxycarbonyl, tert-butoxycarbonyl, benzyloxycarbonyl, p-chlorobenzyloxycarbonyl, p-methylbenzyloxycarbonyl and benzhydryl. Preferred examples of the protecting group for the imino group include substituted oxycarbonyl group such as tert-butoxycarbonyl, benzyloxycarbonyl and p-chlorobenzyloxycarbonyl.

The preparation of salts or reactive derivatives of [II], and of salts of [III], and the introduction of a protecting group into [II] or [III] are easily performed by known processes or processes similar thereto. For the reaction between compound II and compound III, for example, a reactive derivative of starting compound [II] as a substance isolated from a reaction mixture may be reacted with compound III. Alternatively, a reaction mixture as such which contains the reactive derivative of the starting compound [II] which is left unisolated may be reacted with the compound III. A reaction between compound III and compound II, in the case when latter compound is in free acid or in salt form, is effected in the presence of a suitable condensation agent. The condensation agent includes, for example, N,N'-disubstituted carbodiimides such as N,N'-dicyclohexylcarbodiimide, azolides such as N,N'-carbonyldiimidazole, and N,N'-thiocarbonyldiimidazole, dehydrating agents such as N-ethoxycarbonyl-2-ethoxy-1,2-dihydroquinoline, phosphorus oxychloride and alkoxyacetylene and 2-halogenopyridinium salts such as 2-chloropyridiniummethyl iodide and 2-fluoropyridiniummethyl iodide. In the case of using these condensation agents, the reaction is considered to proceed through the reactive derivative of [II]. The reaction of compound II and compound III is usually carried out in a solvent. A suitable solvent is selected from those which do not harm the reaction. Examples of the solvent include ethers such as dioxane, tetrahydrofuran, diethyl ether, tert-butyl methyl ether, diisopropyl ether and ethylene glycol dimethyl ether, esters such as ethyl formate, ethyl acetate and butyl acetate, halogenated hydrocarbons such as dichloromethane, chloroform, carbon tetrachloride, trichlene and 1,2-dichloroethane, hydrocarbons such as n-hexane, benzene and toluene, amides such as formamide, N,N-dimethylformamide and N,N-dimethylacetamide, ketones such as acetone, methyl ethyl ketone and methyl isobutyl ketone, nitriles such as acetonitrile and propionitrile and besides dimethylsulfoxide, sulforan, hexamethylphosphoroamide and water. These may be used alone or as mixed solvents. Preferred examples of the solvent include diethyl ether, toluene, N,N-dimethylformamide, acetonitrile and mixtures thereof. The amount of compound III used is usually 1 to 5 moles, preferably 1 to 3 moles, more preferably 1 to 2 moles per mole of starting compound II.

The reaction is effected at a temperature of $-80°$ to $80°$ C., preferably $-40°$ to $50°$ C., most preferably $-30°$ to $30°$ C. Room temperature ($20°$ to $25°$ C.) may conveniently be employed. Reaction time varies depending on the nature of the starting compounds II and compound III, the nature of the solvent including the mixing ratio in the case of a mixed solvent, and the reaction temperature, but is usually in the range of from 1 minute to 72 hours, preferably from 15 minutes to 36 hours, more preferably from 2 to 24 hours.

In the case when an acid halide of [II] is used as the compound II, the reaction may be effected in the presence of a deoxidizer for the removal of hydrogen halide generated from the reaction system. As the deoxidizer, mention may be made of, for example, inorganic bases such as sodium carbonate, potassium carbonate, calcium carbonate and sodium bicarbonate, tertiary amines such as triethylamine, tripropylamine, tributylamine, diisopropylethylamine, cyclohexyldimethylamine, pyridine, lutidine, γ-collidine, N,N-dimethylaniline, N-methylpiperidine, N-methyl-pyrrolidine and N-methylmorpholine and alkylene oxides such as propylene oxide and epichlorohydrin.

The objective compound I of the present invention is obtained by allowing compound II to react with compound III as mentioned above and, if necessary, elimination of the protecting group and purification. Elimination of the protecting group for the hydroxyl group is effected by the process as it is which is usually employed in the field of the synthesis of peptides. For example, methoxycarbonyl, ethoxycarbonyl, tert-butoxycarbonyl or phenoxycarbonyl is eliminated by acids, for example, hydrochloric acid or trifluoroacetic acid, benzyloxycarbonyl, p-methylbenzyloxycarbonyl or benzhydryloxycarbonyl is eliminated by catalytic reduction, benzyl, p-methylbenzyl, p-methoxybenzyl, p-chlorobenzyl, benzhydryl or trityl is eliminated by acids, for example, trifluoroacetic acid, or catalytic reduction, and trimethylsilyl or tert-butyldimethylsilyl is eliminated by water alone, or in the presence of acetic acid.

When elimination of a protecting group is carried out, the hydroxyl or/and imino group-protected compound I, which has been isolated from a reaction mixture obtained from the reaction of the compound II and the compound III, may be subjected to the elimination of the protecting group. Alternatively, the reaction mixture may be subjected as it is to elimination of a protecting group. Purification of the hydroxyl, amino or/and imino group-protected compound I or the objective compound I is carried out by the known methods such as extraction, gel filtration, ion-exchange resin column chromatography, silica gel thin-layer chromatography, high-performance liquid chromatography and recrystallization. Compound II and compound III are available by known methods or similar methods thereto.

Furthermore, compound I can also be produced by the following process.

Compound I may be produced by reacting a carboxylic acid [IV] of the formula:

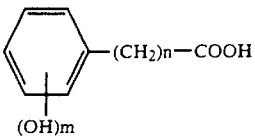

wherein the symbols are the same as defined above, or a salt or a reactive derivative thereof (referred to as "compound IV" hereinafter) with a compound [V] of the formula:

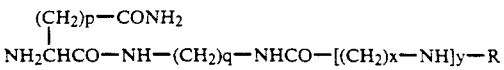

wherein the symbols are the same as defined above, or a salt thereof (referred to as "compound V" hereinafter) and, if necessary, eliminating a protecting group (Reaction formula 2).

Reaction formula 2

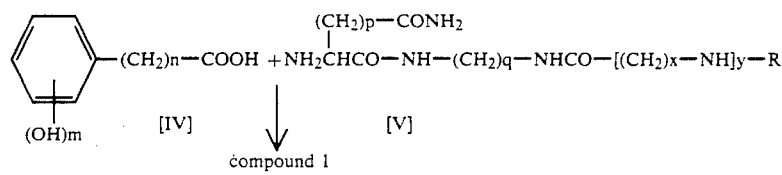

compound 1

In the above formula 2, the starting compound IV may be a salt or a reactive derivative of [IV]. The salt of the compound [IV] includes inorganic base salts and organic base salts as mentioned for salts of compound [II]. The reactive derivative of compound [IV] includes acid halides, acid azides, acid anhydrides, mixed acid anhydrides, active amides, active esters and active thioesters as mentioned for the reactive derivatives of compound [II]. The salt of the starting compound [V] includes salts with organic acids as mentioned in relation of the compound [III]. The hydroxyl group on the benzene ring of the starting compound IV may be protected and the protective group includes protective groups as mentioned for the protective groups of compound II. Furthermore, the imino group (including the amino group in the case of R being a hydrogen atom) of the starting compound IV may be protected and the protective group includes protective groups as mentioned for the protective groups of compound III.

The preparation of salts or reactive derivatives of [IV] and salts of [V] and the introduction of a protecting group into IV or V are easily performed by known processes or processes similar thereto. The reaction between compound IV and compound V is performed under the same reaction conditions (for example, the presence or absence of condensation agent and kind thereof, the kind of solvent, reaction temperature, reaction time, mole number of starting compounds) and treatment conditions after the reaction (for example, for the elimination of the protecting group and the purification) as mentioned for the reaction between compound II and compound III. Compound [IV] and compound [V] are available by known methods or similar methods thereto.

Compound I has a glutamate receptor inhibiting activity. Therefore, compound I is important for research on isolation, structure elucidation and local analysis of the glutamate receptor. Further, the compound I is useful for the elucidation of the mechanism of memory and cranial nerve diseases with which glutamic acid is associated. Accordingly, the compound [I] or a pharmaceutically acceptable salt thereof can be employed as a medicine for therapy or/and for the prevention of the sequelae of cerebral apoplexy in warm-blooded animals, particularly mammals (e.g. human, mouse, rat, cat, dog, rabbit, etc.).

The compound [I] or salt thereof, when used as a medicine, may be administered orally or parenterally as it is, or in the form of a powder, granule, tablet, capsule, solution, suspension, emulsion, suppository or injection, which is prepared according to the conventional methods using pharmaceutically acceptable excipients, vehicles and diluents. The dose varies according to the animal, the symptom, the compound and the administration route; for example, the dose may be about 0.001 mg to 50 mg preferably 1 mg to 5 mg of the compound of this invention per kg of body weight of a warm-blooded animal described above, in the case of oral administration, and may be administered one to three times per day.

The preparations are produced by per se known processes. The above-mentioned oral preparations, for example tablets, are produced by suitable combination with a binder (e.g. hydroxypropylcellulose, hydroxypropylmethylcellulose, macrogol, etc.), a disintegrator (e.g. starch, calcium carboxylmethylcellulose, etc.), or a lubricant (e.g. magnesium stearate, talc, etc.).

The parenteral preparations, for example injections, are produced by suitable combination with an isotonicity factor (e.g. glucose, D-sorbitol, D-mannitol, sodium chloride, etc.), an antisepetic (e.g. benzyl alcohol, chlorobutanol, methyl p-hydroxybenzoate, probyl p-hydroxybenzoate, etc.), or a buffer (e.g. phosphate buffer, sodium acetate buffer, etc.).

The invention is further illustrated by the following specific examples.

EXAMPLE 1

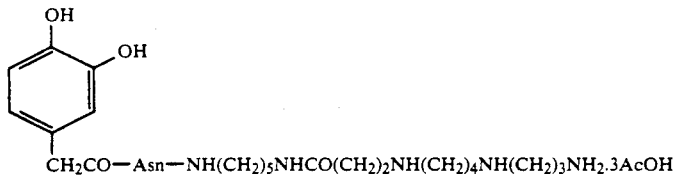

CH$_2$CO—Asn—NH(CH$_2$)$_5$NHCO(CH$_2$)$_2$NH(CH$_2$)$_4$NH(CH$_2$)$_3$NH$_2$·3AcOH

18-[N-(N-3,4-Dihydroxyphenylacetyl)asparaginyl-]amino-4,9,13-triaza-12-oxo-1-aminooctadecane triacetate

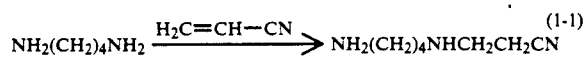

To 1,4-diaminobutane (84.6 g) cooled with ice, acrylonitrile (50.9 g) was added dropwise. After the addition had been completed, the reaction mixture was stirred for 20 minutes under ice cooling, at 40° C. for one hour and at 100° C. for three hours in this order. The resultant mixture was purified by distillation under reduced pressure to obtain as colorless oil 1-(N-2-cyanoethyl)amino-4-aminobutane (66 g).

Boiling point: 120°–121° C./1.7 mmHg.

Elemental analysis for C$_7$H$_{15}$N$_3$: Calcd. C: 59.53; H : 10.71; N : 29.76. Found C: 59.61; H : 10.66; N : 29.62.

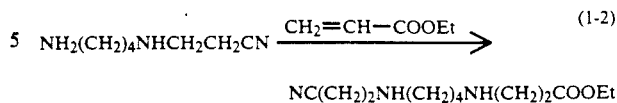

To a solution of 1-(N-2-cyanoethyl)amino-4-aminobutane (62.8 g) in ethanol (200 ml), a solution of ethyl acrylate (48.2 g) in ethanol (200 ml) was added in small portions. The reaction mixture was refluxed under heating for two hours, and then the solvent was distilled off under reduced pressure to obtain as colorless oil 1-(N-2-cyanoethyl)amino-4-(N-2-ethoxycarbonylethyl)aminobutane (108 g).

IR $\nu_{neat}$ (cm$^{-1}$): 1730(C=O), 2260(CN).

Elemental analysis for C$_{12}$H$_{23}$N$_3$O$_2$: Calcd. C: 59.72; H: 9.61; N: 17.41. Found C: 59.64; H: 9.70; N: 17.36.

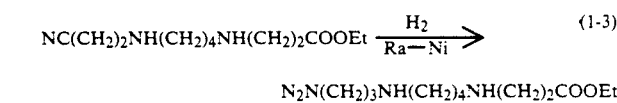

To a solution of 1-(N-2-cyanoethyl)amino-4-(N-ethoxycarbonylethyl)aminobutane (60 g) in ethanol (600 ml), Raney-nickel (30 g) was added and reduction was carried out in an autoclave for 3 hours at the reaction temperature of 25° C. and under the pressure in hydrogen stream of 100 kg/cm$^2$. After the reaction, the catalyst was removed by filtration and the filtrate was concentrated under reduced pressure to obtain as colorless oil 1-(N-3-aminopropyl)amino-4-(N-2-ethoxycarbonylethyl)aminobutane (60 g).

IR $\nu_{neat}$ (cm$^{-1}$): 1725(C=O). NMR δ ppm (CDCl$_3$): 1.26 (t, 3H), 1.2–1.8, (m, 6H), 2.3–3.0 (m, 12H) 4.14 (q, 2H).

Elemental analysis for C$_{12}$H$_{27}$N$_3$O$_2$: Calcd. C: 58.74; H: 11.09; N: 17.13. Found C: 58.80; H: 10.83; N: 16.88.

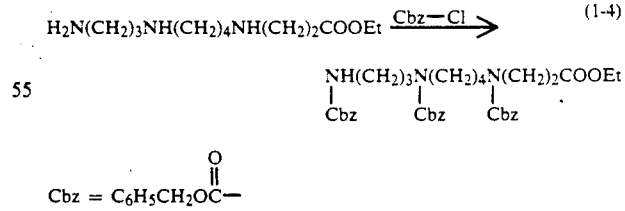

To a solution of 1-(N-3-aminopropyl)amino-4-(N-2-ethoxycarbonylethyl)aminobutane (12.2 g) in dichloromethane (200 ml), triethylamine (28 ml) was added, followed by dropwise addition of benzyloxycarbonyl chloride (Cbz-Cl) (29 ml) in small portions under ice cooling and stirring. The reaction mixture was stirred at room temperature for 12 hours, washed by a saturated aqueous sodium hydrogencarbonate solution and 1N hydrochloric acid solution in this order, and dried over anhydrous magnesium sulfate. Colorless oil obtained by distilling the solvent was purified by a silica gel column chromatography. From fractions eluted with dichloromethane-methanol (20: 1), 1-(N-2-ethoxycarbonylethyl-N-benzyloxycarbonyl)amino-4-[N-3-(N-benzyloxycarbonyl)aminopropyl-N-benzyloxycarbonyl]aminobutane (16.0 g) was obtained as colorless oil.

NMR δ ppm (CDCl$_3$): 1.20 (t, 3H), 1.1–1.8, (m, 6H), 2.53(t, 2H), 2.9–3.6 (m, 10H), 4.27 (q, 2H), 5.10(s, 6H), 7.33(m, 15H).

Elemental analysis for $C_{36}H_{45}N_3O_8$: Calcd. C: 66.75; H: 7.00; N: 6.49. Found C: 66.79; H: 7.12; N: 6.32.

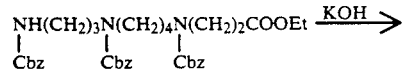

(1-5)

A solution of 1-(N-2-ethoxycarbonylethyl-N-benzyloxycarbonyl)amino-4-[N-3-(N-benzyloxycarbonyl)aminopropyl-N-benzyloxycarbonyl]aminobutane (21 g) in 1N potassium hydroxide-ethanol (68 ml) was stirred at room temperature for 2 hours. Water (100 ml) was added to the reaction mixture, followed by washing twice with diethyl ether (100 ml). The aqueous layer was adjusted to being acidic with 1N hydrochloric acid solution and the resultant was extracted with ethyl acetate. The ethyl acetate layer was washed with water and dried over anhydrous magnesium sulfate. The distillation of ethyl acetate under reduced pressure gave colorless powder of $N^4,N^9,N^{13}$-tribenzyloxycarbonyl-4,9,13-triazatridecanoic acid (16.3 g).

Elemental analysis for $C_{34}H_{41}N_3O_8$: Calcd. C: 65.89; H: 6.67; N: 6.78. Found C: 65.77; H: 6.39; N: 6.60.

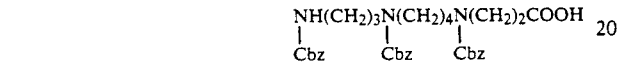

(1-6)

Boc = (CH$_3$)$_3$C—OC—
           ||
           O

To a solution of N-(tert-butoxycarbonyl)cadaverine (2.2 g) and $N^4,N^9,N^{13}$-tribenzyloxycarbonyl-4,9,13-triazatridecanoic acid (6.7 g) in acetonitrile (100 ml), 1-hydroxybenzotriazole (1.46 g) and dicyclohexylcarbodiimide (2.43 g) were added under ice cooling and stirring. The reaction mixture was stirred at room temperature for 12 hours and the precipitated insoluble matter was removed by filtration. The filtrate was concentrated under reduced pressure to give an oily product. The oily product was dissolved in dichloromethane (200 ml), followed by washing with 10% aqueous citric acid solution, a saturated aqueous sodium hydrogencarbonate solution and water in this order. The dichloromethane layer was dried over anhydrous magnesium sulfate. The solvent was distilled under reduced pressure to obtain an oil. The oil was purified by a silica gel column chromatography. From fractions eluted with dichloromethane-methanol (30: 1), 1-(N-benzyloxycarbonyl)amino-18-(N-tert-butoxycarbonyl)amino-$N^4$,$N^9$-dibenzyloxycarbonyl-4,9,13-triaza-12-oxooctadecane (2.8 g) was obtained as colorless oil.

NMR δ ppm (CDCl$_3$): 1.1–1.9(m, 12H), 1.43(s, 9H), 2.37(t, 2H), 2.9–3.7(m, 14H), 5.10(s, 6H), 7.35(m, 15H).

Elemental analysis for $C_{44}H_{61}N_5O_9$: Calcd. C: 65.73; H: 7.65; N: 8.71. Found C: 65.54; H: 7.70; N: 8.50.

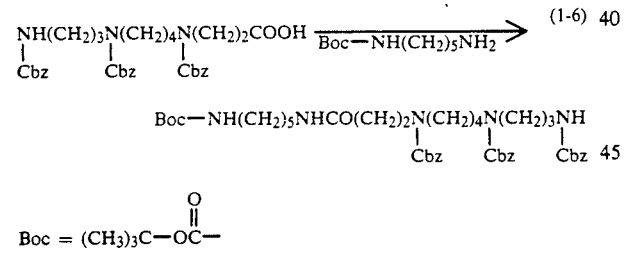

(1-7)

A solution of 1-(N-benzyloxycarbonyl)amino-18-(N-tert-butoxycarbonyl)amino-$N^4$,$N^9$-dibenzyloxycarbonyl-4,9,13-triaza-12-oxooctadecane (2.75 g) in trifluoroacetic acid (10 ml) was stirred at room temperature for 10 minutes, followed by addition of dichloromethane (100 ml). The resultant mixture was adjusted to pH 9.0 with a saturated aqueous sodium hydrogencarbonate solution. The organic layer was separated and dried over anhydrous magnesium sulfate. The solvent was distilled to an obtain oil (2.67 g). This oil was dissolved in acetonitrile (50 ml), followed by addition of N-tert-butoxycarbonyl-L-asparagine (1.19 g), 1-hydroxybenzotriazole (0.92 g) and dicyclohexylcarbodiimide (1.06 g) in this order. The reaction mixture was stirred at room temperature for 5 hours. After the reaction had been completed, the precipitated insoluble matter was removed by filtration. The filtrate was concentrated and the resulting oil was dissolved in ethyl acetate (100 ml), followed by washing with 0.5N hydrochloric acid solution, a saturated aqueous sodium hydrogen carbonate solution and water in this order. The ethyl acetate layer was dried over anhydrous magnesium sulfate. The solvent was distilled and the resultant was purified by reprecipitation with ethyl acetatediethyl ether (1: 2) to obtain 18-[N-(N-tert-butoxycarbonyl)asparaginyl]amino-1-(N-benzyloxycarbonyl)amino-$N^4$,$N^9$-dibenzyloxycarbonyl-4,9,13-triaza-12-oxooctadecane (1.78 g) as colorless powder.

Elemental analysis for $C_{48}H_{67}N_7O_{11}$: Calcd. C: 61.58; H: 7.43; N: 10.48. Found C: 61.43; H: 7.44; N: 10.19.

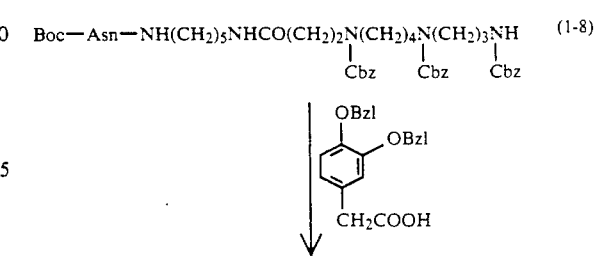

(1-8)

-continued

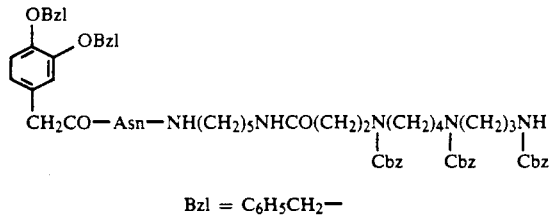

Bzl = C₆H₅CH₂— a) To a solution of 3,4-dibenzyloxyphenylacetic acid (930 mg) in acetonitrile (50 ml), 1-hydroxybenzotriazole (478 mg) and dicyclohexylcarbodiimide (551 mg) were added. The resulting mixture was stirred at room temperature for 2 hours and the precipitate was removed by filtration. The filtrate was concentrated under reduced pressure and to the resultant acetonitrile (20 ml) was added. Insoluble matter was again removed by filtration. The filtrate was used in the following reaction b).

Elemental analysis for $C_{48}H_{67}N_7O_{11}$: Calcd. C: 61.58; H: 7.43; N: 10.48. Found C: 61.43; H: 7.44; N: 10.19.

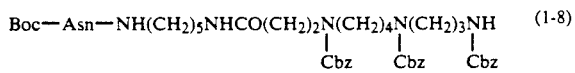 (1-8)

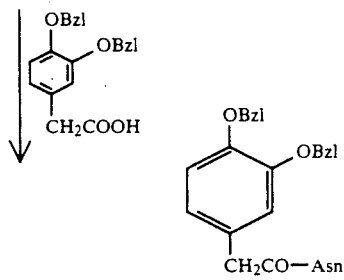

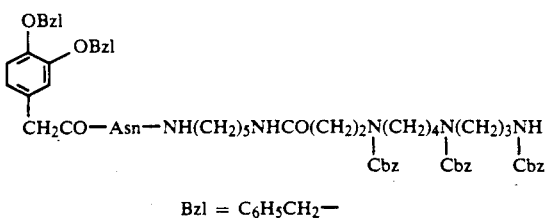

Bzl = C₆H₅CH₂— a) To a solution of 3,4-dibenzyloxyphenylacetic acid (930 mg) in acetonitrile (50 ml), 1-hydroxybenzotriazole (478 mg) and dicyclohexylcarbodiimide (551 mg) were added. The resulting mixture was stirred at room temperature for 2 hours and the precipitate was removed by filtration. The filtrate was concentrated under reduced pressure and to the resultant acetonitrile (20 ml) was added. Insoluble matter was again removed by filtration. The filtrate was used in the following reaction b).

b) 1-(N-Benzyloxycarbonyl)amino-18-[N-(N-tert-butoxycarbonyl)asparaginyl]amino-$N^4,N^9$-benzyloxycarbonyl-4,9,13-triaza-12-oxooctadecane (2.04 g) was dissolved in trifluoroacetic acid (5 ml), followed by stirring at room temperature for 30 minutes. To the reaction mixture, toluene (50 ml) was added and distillation was conducted under reduced pressure. To the resultant diethyl ether was added, followed by stirring, to give white precipitate. This precipitate was collected by filtration, dried and dissolved in acetonitrile (30 ml), followed by addition of triethylamine (0.31 ml) under ice cooling and stirring. To the resulting mixture, N,N-dimethylformamide (2 ml) and the acetonitrile solution obtained in the above a) were added. The reaction mixture was stirred at room temperature for 2 hours. The resulting crystalline powder was collected by filtration and dried to obtain 1-(N-benzyloxycarbonyl)amino-18-[N-(N-3,4-dibenzyloxyphenylacetyl)asparaginyl]amino-$N^4,N^9$-dibenzyloxycarbonyl-4,9,13-triaza-12-oxooctadecane (1.1 g) as colorless crystalline powder.

M.p. 150°–151° C.

Elemental analysis for $C_{65}H_{77}N_7O_{12} \cdot \frac{1}{2}H_2O$: Calcd. C: 67.45; H: 6.79; N: 8.47. Found C: 67.24; H: 6.72; N: 3.45.

(1-9)

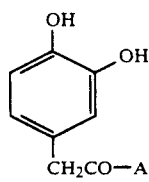

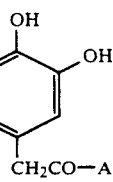

To a solution of the protected form, 1-(N-benzyloxycarbonyl)amino-18-[N-(N-3,4-dibenzyloxyphenylacetyl)asparaginyl]amino-$N^4,N^9$-dibenzyloxycarbonyl-4,9,13-triaza-12-oxooctadecane (970 mg) in methanol (68 ml), acetic acid (0.17 ml) and 10% palladium-carbon (300 mg) were added, and catalytic reduction was carried out for 22 hours at room temperature in a hydrogen stream. The catalyst was removed by filtration and the filtrate was concentrated under reduced pressure to obtain a glassy product. This product was purified by column chromatography using Cephadex LH-20. Fractions eluted with 0.1N acetic acid solution in distilled water were collected and lyophilized to obtain colorless glassy 18-[N-(N-3,4-dihydroxyphenylacetyl)asparaginyl]amino-4,9,13-triaza-12-oxo-1-aminooctadecane triacetate (290 mg).

SIMS: m/z=566[M⁺+H⁺] ($C_{27}H_{47}N_7O_6$: M=565).

EXAMPLE 2

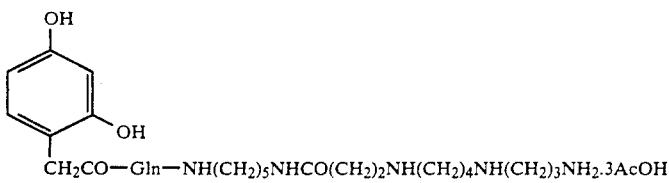

CH₂CO—Gln—NH(CH₂)₅NHCO(CH₂)₂NH(CH₂)₄NH(CH₂)₃NH₂·3AcOH

15

18-[N-(N-2,4-Dihydroxyphenylacetyl)glutaminyl-]amino-4,9,13-triaza-12-oxo-1-aminooctadecane triacetate

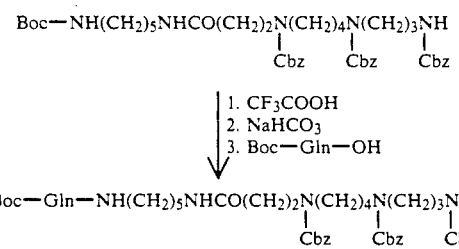

A solution of 1-(N-benzyloxycarbonyl)amino-18-(N-tert-butoxycarbonyl)amino-N⁴,N⁹-dibenzyloxycarbonyl-4,9,13-triaza-12-oxooctadecane (2.0 g) obtained in Example 1-6) in trifluoroacetic acid (3 ml) was stirred for 30 minutes at room temperature, followed by addition of ethyl acetate (50 ml). The resultant mixture was adjusted to pH 9.3 with a saturated aqueous sodium hydrogencarbonate solution. The ethyl acetate layer was separated and dried over anhydrous magnesium sulfate. The solvent was distilled and the resulting glassy product was dissolved in acetonitrile (50 ml). To the resultant solution, N-tert-butoxycarbonyl-L-glutamine (827 mg), 1-hydroxybenzotriazole (602 mg) and dicyclohexylcarbodiimide (693 mg) in this order. The reaction mixture was stirred for 12 hours at room temperature and the precipitated insoluble matter was removed by filtration. The filtrate was concentrated under reduced pressure and the resultant was dissolved in ethyl acetate (100 ml). The ethyl acetate layer was washed with 0.5N hydrochloric acid solution, a saturated aqueous sodium hydrogencarbonate solution and water in this order, and then dried over anhydrous magnesium sulfate. The solvent was distilled to obtain glassy 18-[N-(N-tert-butoxycarbonyl)glutaminyl-]amino-1-(N-benzyloxycarbonyl)amino-N⁴,N⁹-dibenzyloxycarbonyl-4,9,13-triaza-12-oxooctadecane (1.20 g).

Elemental analysis for C₄₉H₆₉N₇O₁₁: Calcd. C: 63.14; H: 7.46; N: 10.52. Found C: 62.87; H: 7.41; N: 10.24.

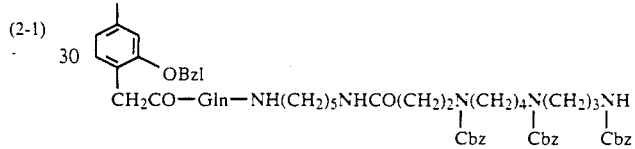

a) To a solution of 2,4-dibenzyloxyphenylacetic acid (495 mg) in acetonitrile (30 ml), 1-hydroxybenzotriazole (254 mg) and dicyclohexylcarbodiimide (293 mg) were added, followed by stirring for 5 hours at room temperature. The resulting precipitate was removed by filtration and the filtrate was concentrated under reduced pressure. To the resultant, acetonitrile (20 ml) was added and insoluble matter was removed by filtration again. The filtrate was used in the following reaction b).

b) 1-(N-Benzyloxycarbonyl)amino-18-[N-(N-tert-butoxycarbonyl)glutaminyl]-amino-N⁴,N⁹-dibenzyloxycarbonyl-4,9,13-triaza-12-oxooctadecane (1.25 g) was dissolved in trifluoroacetic acid (5 ml), followed by stirring for 30 minutes at room temperature. To the reaction mixture, toluene (50 ml) was added, followed by distillation under reduced pressure. To the resultant, diethyl ether was added and under stirring white powder was precipitated. This powder was collected by filtration, dried and dissolved in acetonitrile (16 ml), followed by addition of triethylamine (0.19 ml) under ice cooling and stirring. The resulting mixture, N,N-dimethylformamide (1.5 ml) and the acetonitrile solution obtained in the above a) were added. The reaction mixture was stirred for 12 hours at room temperature, and the precipitated crystalline powder was collected by filtration and dried to obtain as colorless crystalline powder 1-(N-benzyloxycarbonyl)amino-18-[N-(N-2,4-dibenzyloxyphenylacetyl)glutaminyl]amino-N⁴,N⁹-benzyloxycarbonyl-4,9,13-triaza-12-oxooctadecane (378 mg).

M.p. 144°–147° C.

Elemental analysis for C₆₆H₇₉N₇O₁₂·H₂O: Calcd. C: 67.15; H: 6.92; N: 8.31. Found C: 67.21; H: 6.78; N: 8.16.

(2-3)

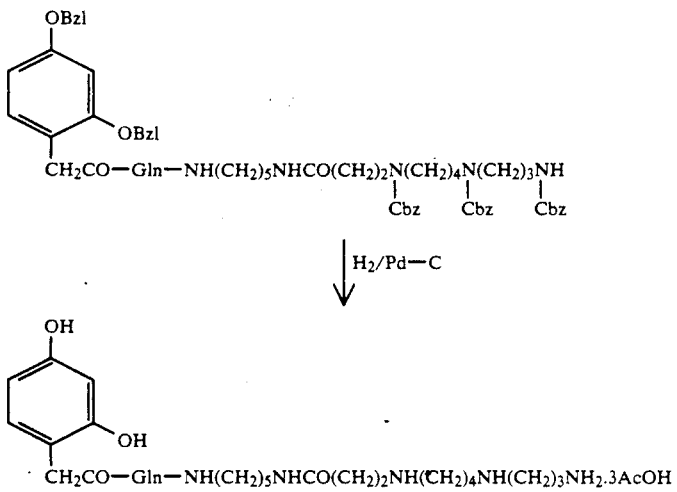

To a solution of a protected form, 1-(N-benzyloxycarbonyl)amino-18-[N-(N-3,4-dibenzyloxyphenylacetyl)glutaminyl]amino-$N^4,N^9$-dibenzyloxycarbonyl-4,9,13-triaza-12-oxooctadecane (350 mg) in methanol (24 ml), acetic acid (0.06 ml) and 10% palladium-carbon (30 mg) were added, and catalytic reduction was carried out for 23 hours at room temperature in a hydrogen stream. Thereafter, treatments were effected in the same manner as in Example 1-9) to obtain as colorless powder 18-[N-(N-2,4-dihydroxyphenylacetyl)-glutaminyl]amino-4,9,13-triaza-12-oxo-1-aminooctadecane triacetate (144 mg).

SIMS: m/z=580[M+ +H+] ($C_{28}H_{49}N_7O_6$: M=579).

EXAMPLE 3 a) To a solution of 3-(2,4-dibenzyloxyphenyl)propionic acid (370 mg) in acetonitrile (20 ml), 1-hydroxybenzotriazole (201 mg) and dicyclohexylcarbodiimide (231 mg) were added, followed by stirring for 3 hours at room temperature. The precipitated insoluble matter was removed by filtration and the filtrate was concentrated under reduced pressure. To the resultant, acetonitrile (20 ml) was added and insoluble matter was removed by filtration again. The filtrate was used in the following reaction b).

b) 1-(N-Benzyloxycarbonyl)amino-18-[N-(N-tert-butoxycarbonyl)asparaginyl]amino-$N^4,N^9$-dibenzyloxycarbonyl-4,9,13-triaza-12-oxooctadecane (850 mg) was dissolved in trifluoroacetic acid (5 ml), followed by stirring for 30 minutes at room temperature. To the reaction mixture, toluene (50 ml) was added and distillation was carried out under reduced pressure. To the resultant, diethyl ether was added and stirred to precipitate colorless crystalline powder. This powder was collected by filtration, dried and dissolved in acetonitrile (30 ml), followed by addition of triethylamine (0.14 ml) under ice cooling and stirring. To the resulting mixture, N,N-dimethylformamide (1.5 ml) and the acetonitrile solution obtained in the above a) were added. The reaction mixture was stirred for 22 hours at room temperature, and the precipitated crystalline powder was collected by filtration and dried to obtain 1-(N-benzyloxycarbonyl)amino-18-[N-[N-3-(2,4-dibenzyloxyphenyl)propionyl]asparaginyl]amino-$N^4,N^9$-dibenzyloxycarbonyl-4,9,13-triaza-12-oxooctadecane (340 mg).

M.p. 138°–140° C.

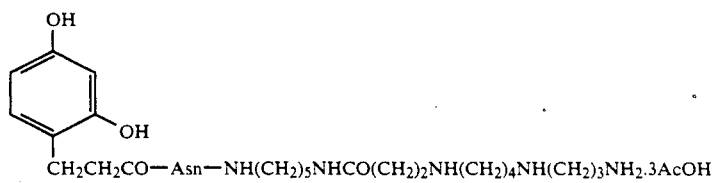

18-[N-[N-3-(2,4-Dihydroxyphenyl)propionyl]asparaginyl]amino-4,9,13-triaza-12-oxo-1-aminooctadecane triacetate

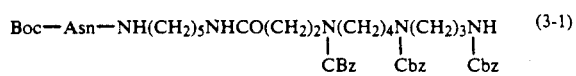

(3-1)

1. CF$_3$COOH
2. 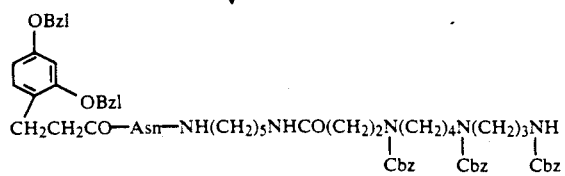

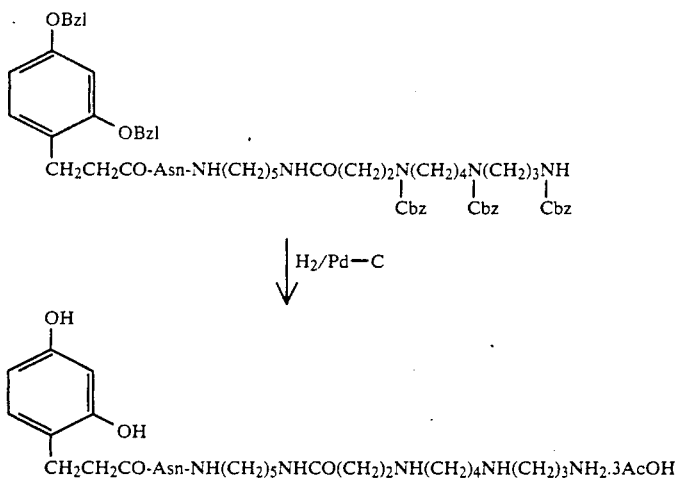

(3-2)

To a solution of a protected form, 1-(N-benzyloxycarbonyl)amino-18-[N-[3-(2,4-dibenzyloxyphenyl)propionyl]asparaginyl]amino-$N^4$,$N^9$-dibenzyloxy-4,9,13-triaza-12-oxooctadecane (328 mg) in methanol (50 ml), acetic acid (0.05 ml) and 10% palladium-carbon (50 mg) were added, and catalytic reduction was carried out for 24 hours at room temperature in a hydrogen stream. Thereafter, treatments were effected in the same manner as in Example 1-9) to obtain as colorless powder 18-[N-[N-3-(2,4-dihydroxyphenyl)propionyl]asparaginyl]amino-4,9,13-triaza-12-oxo-1-aminooctadecane triacetate (93 mg).

SIMS: m/z=580[$M^+ + H^+$] ($C_{28}H_{49}N_7O_6$: M=579).

EXAMPLE 4

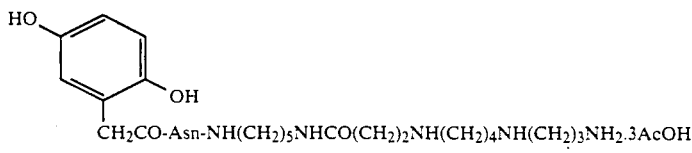

18-[N-(N-2,5-Dihydroxyphenylacetyl)asparaginyl-]amino-4,9,13-triaza-12-oxo-1-aminooctadecane triacetate

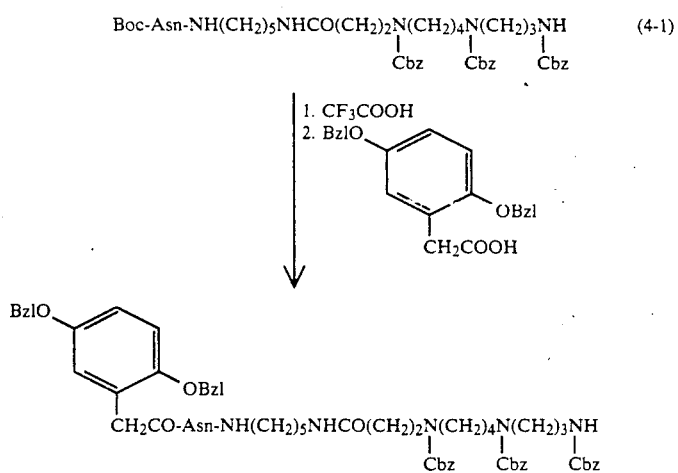

(4-1)

a) To a solution of 2,5-dibenzyloxyphenylacetic acid (116 mg) in acetonitrile (7 ml), 1-hydroxybenzotriazole (60 mg) and dicyclohexylcarbodiimide (69 mg) were added, followed by stirring for 4 hours at room temperature. The resulting precipitate was removed by filtration and the filtrate was concentrated under reduced pressure. To the resultant, acetonitrile (10 ml) was added and insoluble matter was removed by filtration again. The filtrate was used in the following reaction b).

b) 1-(N-Benzyloxycarbonyl)amino-18-[N-(N-tert-butoxycarbonyl)asparaginyl]amino-$N^4$,$N^9$-dibenzyloxycarbonyl-4,9,13-triaza-12-oxooctadecane (313 mg) obtained in Example 1-7) was dissolved in trifluoroacetic acid (1 ml), followed by stirring for 30 minutes at room temperature. To the reaction mixture, toluene (30 ml) was added and distillation was carried out under reduced pressure. To the resultant, diethyl ether was added and after stirring powder was precipitated. The powder was collected by filtration, dried and dissolved in acetonitrile (5 ml), followed by addition of triethylamine (0.05 ml) under ice cooling and stirring. To the resulting mixture, N,N-dimethylformamide (1.5 ml) and then the acetonitrile solution obtained in the above a) were added. The reaction mixture was stirred for 12 hours at room temperature, and the precipitated crystalline powder was collected by filtration and dried to obtain as colorless crystalline powder 1-(N-benzyloxycarbonyl)amino-18-[N-(N-2,5-dibenzyloxyphenylacetyl)asparaginyl]amino-$N^4$,$N^9$-dibenzyloxycarbonyl4,9,13-triaza-12-oxooctadecane (143 mg).

M.p. 150°-152° C.

Elemental analysis for $C_{65}H_{77}N_7O_{12} \cdot H_2O$: Calcd. C: 66.93; H: 6.83; N: 8.41. Found C: 66.76; H: 6.82; N: 8.07.

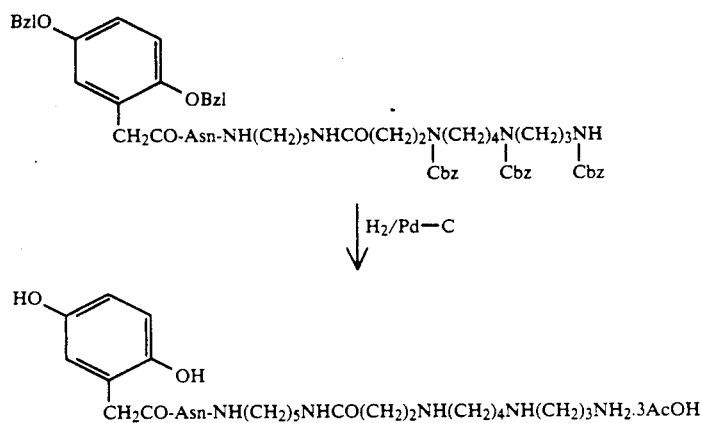

To a solution of 1-(N-benzyloxycarbonyl)amino-18-[N-(N-2,5-dibenzyloxyphenylacetyl)asparaginyl]amino-$N^4$,$N^9$-dibenzyloxycarbonyl-4,9,13-triaza-12-oxooctadecane (130 mg) in methanol (10 ml), acetic acid (0.02 ml) and 10% palladium-carbon (20 mg) were added, and catalytic reduction was carried out for 23 hours at room temperature in hydrogen stream. Thereafter, treatments were effected in the same manner as in Example 1-9) to obtain 18-[N-(N-2,5-dihydroxyphenylacetyl)asparaginyl]amino-4,9,13-triaza-12-oxo-1-aminooctadecane triacetate (30 mg).

SIMS: m/z=566[$M^+ + H^+$] ($C_{27}H_{47}N_7O_6$: M=565).

EXAMPLE 5

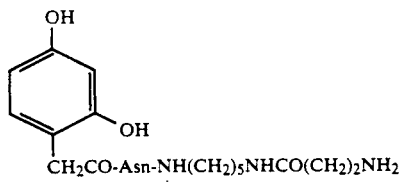

9-[N-(N-2,4-Dihydroxyphenylacetyl)asparaginyl]amino-4-aza-3-oxo-1-aminononane

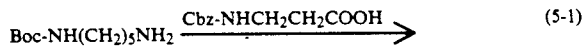

To a solution of 1-amino-5-(N-tert-butoxcarbonyl)aminopentane (4.0 g) in N,N-dimethylformamide (20 ml), N-benzyloxycarbonyl-β-alanine (4.42 g), 1-hydroxybenzotriazole (2.68 g) and dicyclohexylcarbodiimide (4.09 g) in this order were added. Thereafter, treatments were effected in the same manner as in Example 1-7) to obtain as colorless powder 9-(N-tert-butoxycarbonyl)amino-1-(N-benzyloxycarbonyl)amino-4-aza-3-oxononane (3.50 g).

Elemental analysis for $C_{21}H_{33}N_3O_5$: Calcd. C: 61.89; H: 8.16; N: 10.31. Found C: 61.76; H: 8.30; N: 10.04.

Boc-NH(CH$_2$)$_5$NHCO(CH$_2$)$_2$NH-Cbz     (5-2)

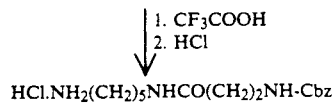

HCl·NH$_2$(CH$_2$)$_5$NHCO(CH$_2$)$_2$NH-Cbz

A solution of 9-(N-tert-butoxycarbonyl)amino-1-(N-benzyloxycarbonyl)amino-4-aza-3-oxononane (3.50 g) in trifluoroacetic acid (20 ml) was stirred for 10 minutes at room temperature. Trifluoroacetic acid was distilled off under reduced pressure and to the resultant, 1N hydrochloric acid-dioxane solution (10 ml) was added. Dioxane was distilled off and to the resultant diethyl ether was added, followed by stirring, to obtain powder. This powder was collected by filtration and dried to obtain 9-amino-1-(N-benzyloxycarbonyl)amino-4-aza-3-oxononane monohydrochloride (2.77 g).

Elemental analysis for $C_{16}H_{25}N_3O_3 \cdot HCl$: Calcd. C: 55.88; H: 7.62; N: 12.22. Found C: 55.80; H: 7.77; N: 11.96.

HCl·NH$_2$(CH$_2$)$_5$NHCO(CH$_2$)$_2$NH-Cbz     (5-3)

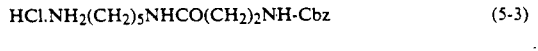

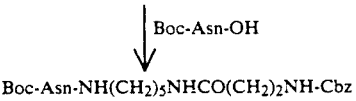

Boc-Asn-NH(CH$_2$)$_5$NHCO(CH$_2$)$_2$NH-Cbz

To a solution of 9-amino-1-(N-benzyloxycarbonyl)amino-4-aza-3-oxononane monohydrochloride (3.43 g) in N,N-dimethylformamide (30 ml), N-tert-butoxycarbonylasparagine (2.32 g), triethylamine (1.54 ml), 1-hydroxybenzotriazole (1.35 g) and dicyclohexylcarbodiimide (2.17 g) in this order were added under stirring. The reaction mixture was stirred for 12 hours. Thereafter, treatments were effected in the same manner as in Example 1-7) to obtain as colorless powder 9-[N-(N-tert-butoxycarbonyl)asparaginyl]amino-1-(N-benzyloxycarbonyl)amino-4-aza-3-oxononane (5.0 g).

Elemental analysis for $C_{25}H_{39}N_5O_7$: Calcd. C: 57.56; H: 7.54; N: 13.43. Found C: 57.49; H: 7.70; N: 13.14.

Boc-Asn-NH(CH₂)₅NHCO(CH₂)₂NH-Cbz     (5-4)

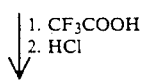

HCl.H-Asn-NH(CH₂)₅NHCO(CH₂)₂NH-Cbz

A solution of 9-[N-(N-tert-butoxycarbonyl)asparaginyl]amino-1-(N-benzyloxycarbonyl)amino-4-aza-3-oxononane (4.18 g) in trifluoroacetic acid (20 ml) was stirred for 30 minutes at room temperature. Thereafter, treatments were effected in the same manner as in Example 5-2) to obtain as colorless powder 9-(N-asparaginyl)amino-1-(N-benzyloxycarbonyl)amino-4-aza-3-oxononane monohydrochloride (3.51 g).

Elemental analysis for C₂₀H₃₁N₅O₅.HCl: Calcd. C: 52.45; H: 7.04; N: 15.29. Found C: 52.39; H: 6.88; N: 15.03.

HCl.H-Asn-NH(CH₂)₅NHCO(CH₂)₂NH-Cbz     (5-5)

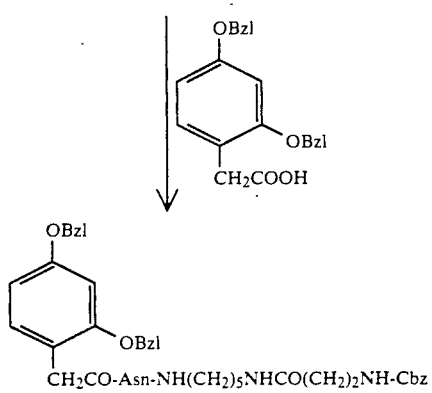

To a solution of 9-(N-asparaginyl)amino-1-(N-benzyloxycarbonyl)amino-4-aza-3-oxononane monohydrochloride (386 mg) in N,N-dimethylformamide (10 ml), 2,4-dibenzyloxyphenylacetic acid (510 mg), triethylamine (0.16 ml), 1-hydroxybenzotriazole (150 mg) and dicyclohexylcarbodiimide (250 mg) in this order were added under stirring. After the reaction mixture was stirred for 12 hours at room temperature, treatments were effected in the same manner as in Example 5-3) to obtain as colorless crystal 9-[N-(N-2,4-dibenzyloxyphenylacetyl)asparaginyl]amino-1-(N-benzyloxycarbonyl)amino-4-aza-3-oxononane (364 mg).

M.p. 183°–184° C.

Elemental analysis for C₄₂H₄₉N₅O₈: Calcd. C: 67.09; H: 6.57; N: 9.32. Found C: 66.80; H: 6.43; N: 9.08.

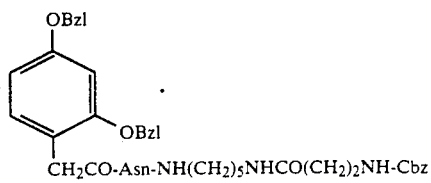     (5-6)

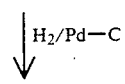

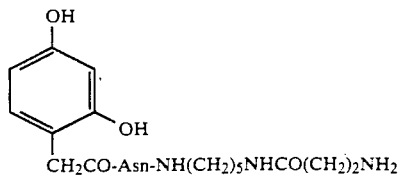

To a solution of 9-[N-2,4-dibenzyloxyphenylacetyl)asparaginyl]amino-1-(N-benzyloxycarbonyl)amino-4-aza-3-oxononane (320 mg) in methanol (20 ml), 10% palladium-carbon (50 mg) was added, and catalytic reduction was carried out for 20 hours at room temperature in a hydrogen stream. Thereafter, treatments were effected in the same manner as in Example 1-9) to obtain as colorless powder 9-[N-(N-2,4-dihydroxyphenylacetyl)asparaginyl]amino-4-aza-3-oxo-1-aminononane (160 mg).

Elemental analysis for C₂₀H₃₁N₅O₆.½H₂O: Calcd. C: 53.80; H: 7.22; N: 15.69. Found C: 53.90; H: 7.50; N: 15.46.

EXAMPLE 6

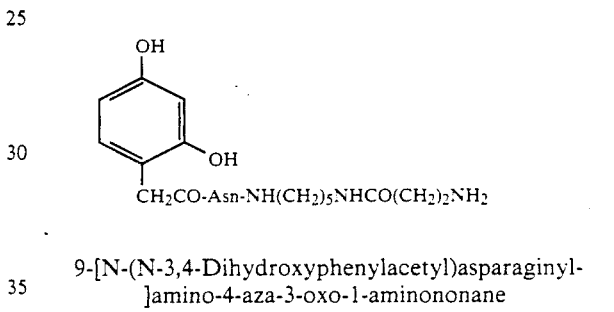

9-[N-(N-3,4-Dihydroxyphenylacetyl)asparaginyl]amino-4-aza-3-oxo-1-aminononane

HCl.H-Asn-NH(CH₂)₅NHCO(CH₂)₂NH-Cbz     (6-1)

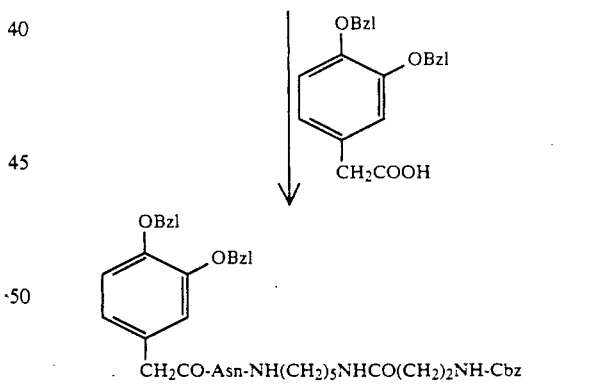

To a solution of 9-(N-asparaginyl)amino-1-(N-benzyloxycarbonyl)amino-4-aza-3-oxononane (642 mg) obtained in Example 5-4) in N,N-dimethylformamide (10 ml), 3,4-dibenzyloxyphenylacetic acid (435 mg), triethylamine (0.22 ml), 1-hydroxybenzotriazole (189 mg) and dicyclohexylcarbodiimide (383 mg) in this order were added under stirring. After the reaction mixture was stirred for 12 hours at room temperature, treatments were effected in a the same manner as in Example 5-3) to obtain as colorless powder 9-[N-(N-3,4-dibenzyloxyphenylacetyl)asparaginyl]amino-1-(N-benzyloxycarbonyl)amino-4-aza-3-oxononane (600 mg).

Elemental analysis for C₄₂H₄₉N₅O₈: Calcd. C: 67.09; H: 6.57; N: 9.32. Found C: 66.79; H: 6.41; N: 9.12.

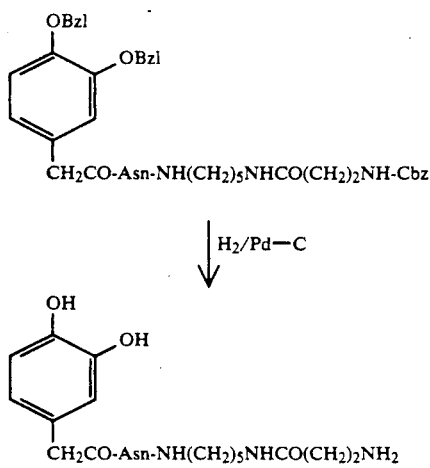

(6-2)

To a solution of 9-[N-(N-3,4-dibenzyloxyphenylacetyl)asparaginyl]amino-1-(N-benzyloxycarbonyl)amino-4-aza-3-oxononane (420 mg) in methanol (20 ml), 10% palladium-carbon (56 mg) was added, and catalytic reduction was carried out for 20 hours at room temperature in hydrogen stream. Thereafter, treatments were effected in the same manner as in Example 1-9) to obtain as colorless crystal 9-[N-(N-3,4-dihydroxyphenylacetyl)asparaginyl]amino-4-aza-3-oxo-1-aminononane (176 mg).

M.p. 88°–91° C.

Elemental analysis for $C_{20}H_{31}N_5O_6$: Calcd. C: 54.91; H: 7.14; N: 16.01. Found C: 55.12; H: 7.23; N: 15.83.

EXAMPLE 7

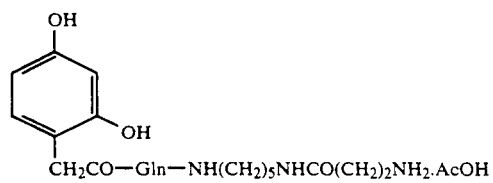

9-[N-(N-2,4-Dihydroxyphenylacetyl)glutaminyl]amino-4-aza-3-oxo-1-aminononane monoacetate

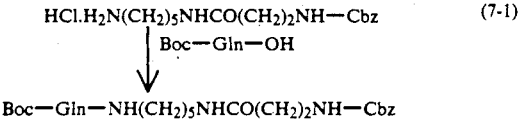

(7-1)

To a solution of 9-amino-1-(N-benzyloxycarbonyl)amino-4-aza-3-oxononane monohydrochloride (1.10 g) obtained in Example 5-2) in N,N-dimethylformamide (20 ml), N-tert-butoxycarbonylglutamine (1.18 g), triethylamine (0.52 ml), 1-hydroxybenzotriazole (650 mg) and dicyclohexylcarbodiimide (990 mg) in this order were added under stirring. After the reaction mixture was stirred for 12 hours at room temperature, treatments were effected in the same manner as in Example 1-7) to obtain as colorless powder 9-[N-(N-tert-butoxycarbonyl)glutaminyl]amino-1-(N-benzyloxycarbonyl)amino-4-aza-3-oxononane (700 mg).

Elemental analysis for $C_{26}H_{41}N_5O_7 \cdot H_2O$: Calcd. C: 56.40; H: 7.83; N: 12.65. Found C: 56.33; H: 7.70; N: 12.41.

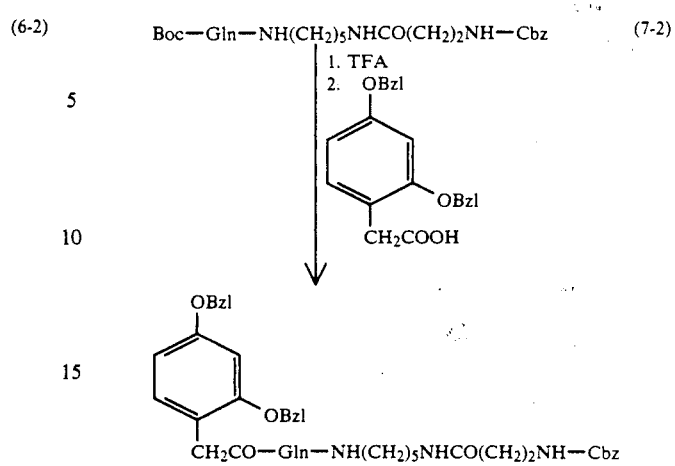

(7-2)

A solution of 9-[N-(N-tert-butoxycarbonyl)glutaminyl]amino-1-(N-benzyloxycarbonyl)amino-4-aza-3-oxononane (670 mg) in trifluoroacetic acid was stirred for 10 minutes at room temperature. Thereafter, treatments were effected in the same manner as in Example 5-2) to obtain as colorless powder 9-(N-glutaminyl)amino-1-(N-benzyloxycarbonyl)amino-4-aza-3-oxononane monohydrochloride (460 mg).

To a solution of this powder in N,N-dimethylformamide (20 ml), 2,4-dibenzyloxyphenylacetic acid (470 mg), triethylamine (0.19 ml), 1-hydroxybenzotriazole (182 mg) and dicyclohexylcarbodiimide (257 mg) in this order were added under stirring. After the reaction mixture was stirred for 12 hours at room temperature, treatments were effected in the same manner as in Example 5 -3) to obtain as colorless crystal 9-[N-(N-2,4-benzyloxyphenylacetyl)glutaminyl]amino-1-(N-benzyloxycarbonyl)amino-4-aza-3-oxononane (620 mg).

M.p. 217°–219° C.

Elemental analysis for $C_{43}H_{51}N_5O_8$: Calcd. C: 67.43; H: 6.71; N: 9.15. Found C: 67.60; H: 6.49; N: 8.83.

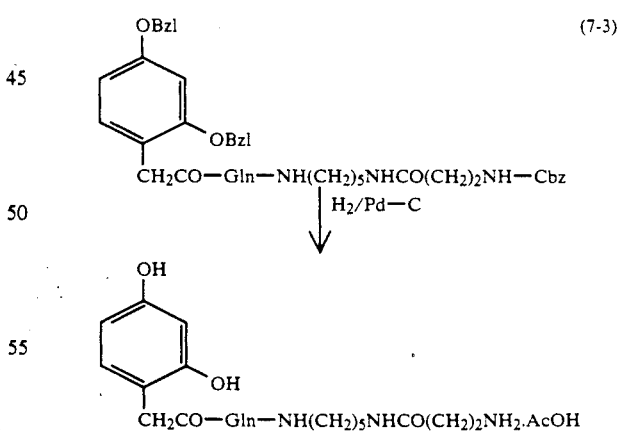

(7-3)

To a solution of 9-[N-(N-2,4-dibenzyloxyphenylacetyl)glutaminyl]amino-1-(N-benzyloxycarbonyl)amino-4-aza-3-oxononane (0.57 g) in methanol (10 ml), acetic acid (0.1 ml) and 10% palladium-carbon (50 mg) were added, and catalytic reduction was carried out for 20 hours at room temperature in hydrogen stream. Thereafter, treatments were effected in the same manner as in Example 1-9) to obtain as colorless powder 9-[N-(N-2,4-dihydroxyphenylacetyl)- glutaminyl]amino-4-aza-3-oxo-1-aminononane monoacetate (380 mg).

Elemental analysis for C₂₁H₃₃N₅O₆·CH₃COOH·H₂O: Calcd. C: 52.16; H: 7.42; N: 13.23. Found C: 52.40; H: 7.29; N: 12.98.

EXAMPLE 8

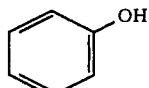

9-[N-(N-3-Hydroxyphenylacetyl)asparaginyl]amino-4-aza-3-oxo-1-aminononane

 (8-1)

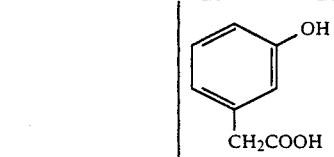

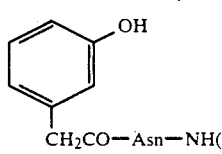
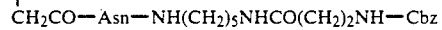

To a solution of 9-(N-asparaginyl)amino-1-(N-benzyloxycarbonyl)amino-4-aza-3-oxononane (642 mg) obtained in Example 5-4) in N,N-dimethylformamide (10 ml), 3-hydroxyphenylacetic acid (213 mg), triethylamine (0.22 ml), 1-hydroxybenzotriazole (189 mg) and dicyclohexylcarbodiimide (383 mg) in this order were added under stirring. After the reaction mixture was stirred for 12 hours at room temperature, treatments were effected in the same manner as in Example 5-3) to obtain as colorless powder 9-[N-(N-3-hydroxyphenylacetyl)asparaginyl]amino-1-(N-benzyloxycarbonyl)amino-4-aza-3-oxononane (530 mg).

Elemental analysis for C₂₈H₃₇N₇O₅: Calcd. C: 60.52; H: 6.71; N: 12.61. Found C: 60.33; H: 6.89; N: 12.48.

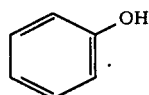 (8-2)
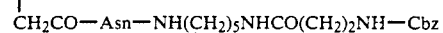
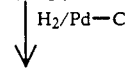
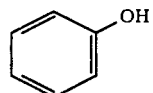
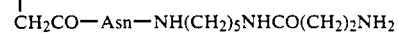

To a solution of 9-[N-(N-3-hydroxyphenylacetyl)asparaginyl]amino-1-(N-benzyloxycarbonyl)amino-4-aza-3-oxononane (470 mg) in methanol (10 ml), 10% palladium-carbon (50 mg) was added, and catalytic reduction was carried out at room temperature in hydrogen stream. The reaction mixture was treated in the same manner as in Example 1-9) to obtain as colorless crystal 9-[N-(N-3-hydroxyphenylacetyl)asparaginyl]amino-4-aza-3-oxononane (310 mg).

M.p. 114°–115° C.

Elemental analysis for C₂₀H₃₁N₅O₅: Calcd. C: 56.99; H: 7.14; N: 16.62. Found C: 56.74; H: 7.03; N: 16.31.

EXAMPLE 9

In the same manner as in Example 8, compounds of Table-1 were obtained.

TABLE 1

CH₂CO—Asn—NH(CH₂)₅NHCO(CH₂)₂NH₂ (with R-substituted phenyl)

| R | m.p. (°C.) | molecular formula | Elemental analysis Calcd. (Found) | | |
|---|---|---|---|---|---|
| | | | C | H | N |
| 2-OH | 82–85 | C₂₀H₃₁N₅O₅ | 56.99 (56.90) | 7.14 (6.88) | 16.62 (16.39) |
| 4-OH | 180–183 | C₂₀H₃₁N₅O₅ | 56.99 (57.20) | 7.14 (7.38) | 16.62 (16.40) |
| 2,5-di-OH | crystalline powder | C₂₀H₃₁N₅O₆ | 54.91 (54.68) | 7.14 (7.00) | 16.01 (15.73) |

REFERENCE EXAMPLE 1

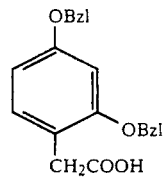

2,4-Dibenzyloxyphenylacetic acid

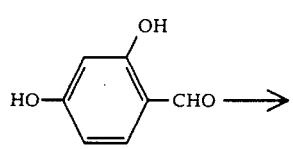

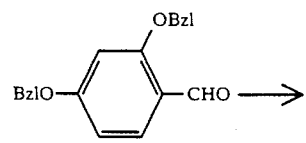

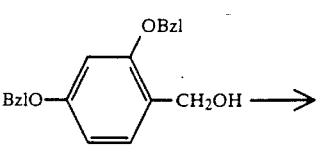

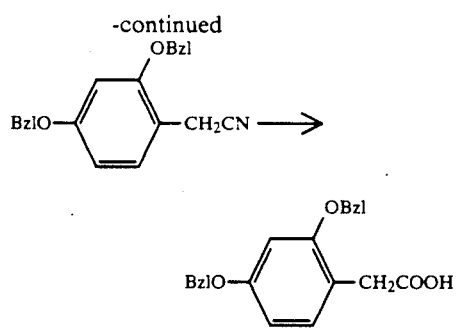

(i) 2,4-Dihydroxybenzaldehyde (14.5 g) was dissolved in ethanol (60 ml) and then thereto were added benzyl chloride (30 ml) and sodium carbonate (1.7 g), followed by reflux under heating for 5 hours. Insoluble matters were removed by filtration. The filtrate was allowed to stand for cooling and then the produced solid was collected by filtration and recrystallized from ethanol to obtain 2,4-dibenzyloxybenzaldehyde (20 g, yield 60%). Melting point: 89°–90° C.

(ii) 2,4-Dibenzyloxybenzaldehyde (20 g) was dissolved in methanol (700 ml) and then thereto was added sodium borohydride (3.6 g) and this was left to stand at room temperature (20° C.) for 1.5 hours. To the reaction mixture was added water (1.5 l) and the resulting precipitate was collected by filtration and recrystallized from ethanol to obtain 2,4-dibenzyloxybenzyl alcohol (19.8 g, yield 98%). Melting point; 84°–85° C.

(iii) 2,4-Dibenzyloxybenzyl alcohol (19.8 g) was dissolved in anhydrous benzene (150 ml) and then thereto was added thionyl chloride (40 g), followed by reflux under heating for 1 hour. This was concentrated to dryness under reduced pressure to obtain crude 2,4-dibenzyloxybenzyl chloride. This product was used for the subsequent reaction without purification.

(iv) The above obtained crude 2,4-dibenzyloxybenzyl chloride was dissolved in dimethyl sulfoxide (150 ml) and then thereto was added sodium cyanide (4 g), followed by stirring for 2 hours at room temperature (20° C.). The reaction mixture was added to water (1 l) and extracted with dichloromethane (1 l). The dichloromethane extract was concentrated under reduced pressure and the residue was purified by a silica gel column (inner diameter: 10 cm, length 50 cm; developer: dichloromethane-n-hexane 1:1 (v/v) mixed solution) and furthermore, was recrystallized from diethyl ether-n-hexane 2:1 (v/v) mixed solution to obtain 2,4-dibenzyloxyphenylacetonitrile (14.3 g, yield 70% from 2,4-dibenzyloxybenzyl alcohol). Melting point: 99°–100° C.

(v) 2,4-Dibenzyloxyphenylacetonitrile (14.3 g) was dissolved in ethanol (250 ml) and then, thereto was added an aqueous potassium hydroxide solution (prepared by dissolving 32 g of potassium hydroxide in 80 ml of water), followed by reflux under heating for 15 hours. The reaction mixture was concentrated under reduced pressure and then dissolved in water (100 ml). The solution was made acidic with concentrated hydrochloric acid and extracted with dichloromethane. The dichloromethane extract was dried over anhydrous magnesium sulfate and concentrated under reduced pressure. Thereafter, the residue was subjected to separation and purification by a silica gel column (inner diameter: 10 cm, length: 50 cm; developer: dichloromethane-ethyl acetate 4:1 (v/v) mixed solution). Thus separated and purified product was recrystallized from benzene to obtain 2,4-dibenzyloxyphenylacetic acid (14.4 g, yield 95%). Melting point: 139° C.

REFERENCE EXAMPLE 2

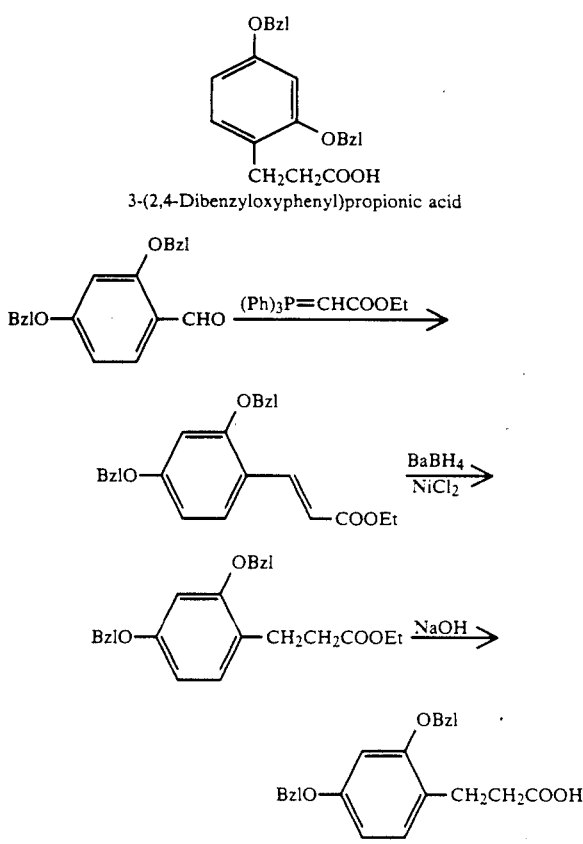

(i) To a solution of 2,4-dibenzyloxybenzaldehyde (702 mg) in toluene (30 ml), ethoxycarbonylmethylenetriphenylphosphoran (1.0 g) was added, followed by reflux under heating for 2.5 hours. After the reaction mixture was allowed to stand for cooling, the solvent was distilled off and the residue was purified by a silica gel column chromatography. From the fraction eluted with dichloromethane was obtained ethyl 3-(2,4-dibenzyloxyphenyl)-2-propenoate (794 mg) as an oily product.

Elemental analysis for $C_{25}H_{24}O_4$: Calcd. C: 77.30; H: 6.23. Found C: 77.28; H: 630.

NMR δ ppm(CDCl$_3$): 1.27(t, 3H), 4.20(q, 2H), 5.00(s, 2H), 5.08(s, 2H), 6.46–6.63(m, 3H), 7.10–7.50(m, 5H), 7.67–7.80(d, 1H), 7.86–8.05(d, 1H)

(ii) Sodium borohydride (10 mg) was added to an ethanolic solution (100 ml) of nickel chloride (100 mg), followed by stirring for 5 minutes. Then, thereto was added ethyl 3-(2,4-dihydroxyphenyl)-2-propenoate (780 mg), followed by addition of sodium borohydride (100 mg) in small portions under ice cooling and stirring. After the reaction terminated, 5N hydrochloric acid solution (0.2 ml) was added and the precipitated insoluble matter was removed by filtration. Ethanol was distilled off and the resultant was dissolved in dichloromethane. The dichloromethane solution was washed with water and dried over anhydrous sodium sulfate. Dichloromethane was distilled off to obtain ethyl 3-(2,4-dibenzyloxyphenyl)propionate (750 mg) as colorless oil.

Elemental analysis for $C_{25}H_{26}O_4$:
Calcd. C: 76.90; H: 6.71.

Found C: 76.78; H: 6.84.

NMR δ ppm(CDCl₃): 1.18(t, 3H), 2.45-3.05(m, 4H), 4.07(q, 2H), 4.97(s, 2H), 5.01(s, 2H), 6.38-7.50(m, 13H)

(iii) To a solution of ethyl 3-(2,4-dibenzyloxyphenyl)-propionate (12.0 g) in ethanol (300 ml), sodium hydroxide (10.3 g) was added, followed by stirring at room temperature for 6 hours. The reaction mixture was adjusted to pH 4.0 with addition of 5N hydrochloric acid solution. Ethanol was distilled off and to the residue was added water. The precipitated crystal was collected by filtration, washed with water and dried to obtain as colorless crystal 3-(2,4-dibenzyloxyphenyl)-propionic acid (9.4 g).

M.p. 125°-127.5° C.

Elemental analysis for $C_{23}H_{22}O_4$: Calcd. C: 76.22; H: 6.12. Found C: 76.37; H: 6.30.

NMR δ ppm(CDCl₃): 2.47-3.03(m, 4H), 4.97(s, 2H), 5.02(s, 2H), 6.40-7.53(m, 13H).

REFERENCE EXAMPLE 3

Boc—NH(CH₂)₅NH₂

5-(N-tert-Butoxycarbonyl)amino-1-aminopentane (N-tert-butoxycarbonylcadaverine)

NH₂(CH₂)₅OH ⟶ Boc—NH(CH₂)₅OH ⟶

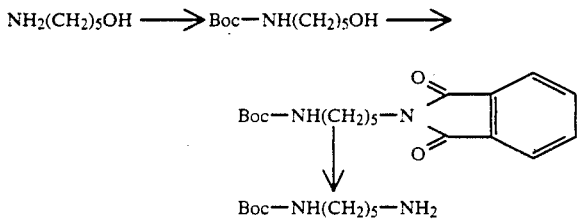

Boc—NH(CH₂)₅—NH₂ i) To a solution of 5-amino-1-pentanol (10 g) in dioxane (50 ml), tert-butyl 4,6-dimethylpyrimidin-2-ylthiolcarbonate (Boc-SDP)(23.31 g) was added, followed by stirring at room temperature for 12 hours. The solvent was distilled off and the resultant was dissolved in ethyl acetate (300 ml). The ethyl acetate solution was washed with 1N hydrochloric acid solution and dried over anhydrous sodium sulfate. The solvent was distilled off to obtain as colorless oil 5-(N-tert-butoxycarbonyl)amino-1-pentanol (14.3 g).

Elemental analysis for $C_{10}H_{21}NO_3$: Calcd. C: 66.90; H: 8.42; N: 5.57. Found C: 66.77; H: 8.19; N: 5.36.

ii) To a solution of 5-(N-tert-butoxycarbonyl)amino-1-pentanol (21.3 g) in anhydrous tetrahydrofuran (300 ml), triphenylphosphine (54.9 g), phthalimide (30.8 g) and dimethylazodiformate (30.6 g) were added under ice cooling and stirring. The reaction mixture was stirred at room temperature for 3 hours. The solvent was distilled off under reduced pressure and the resultant was extracted with n-hexane-ethyl acetate (2: 1). The organic layer was concentrated under reduced pressure to obtain colorless oil. The oil was purified by a silica gel column chromatography. From fractions eluted with n-hexane-ethyl acetate (2: 1), N-[5-(N-tert-butoxycarbonyl)amino]pentylphthalimide (22.5 g) was obtained.

M.p. 81°-83° C.

Elemental analysis for $C_{18}H_{24}N_2O_4$: Calcd. C: 65.04; H: 7.28; N: 8.43. Found C: 64.87; H: 7.02; N: 8.70.

iii) To a solution of N-[5-(N-tert-butoxycarbonyl)amino]pentylphthalimide (21.5 g) in methanol (500 ml), hydrazine hydrate (20 ml) was added, followed by stirring for 4 hours under heating at 80° C. The precipitated crystal was removed by filtration and the filtrate was concentrated under reduced pressure to obtain as colorless oil 5-(N-tert-butoxycarbonyl)amino-1-aminopentane (11.9 g).

Elemental analysis for $C_{10}H_{22}N_2O_2$: Calcd. C: 59.37; H: 10.96; N: 13.85. Found C: 59.10; H: 10.71; N: 13.79.

REFERENCE EXAMPLE 4

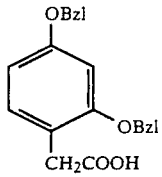

3,4-Dibenzyloxyphenylacetic acid i) To a solution of 3,4-dihydroxyphenylacetic acid (10 g) in N,N-dimethylformamide (50 ml), potassium carbonate (74 g) and benzyl bromide (37 g) were added, followed by stirring at 40° C. for 6 hours. The solvent was distilled off and the resultant was extracted with dichloromethane. The dichloromethane extract was washed with water and then dried over anhydrous sodium sulfate. The solvent was distilled off to obtain as colorless crystal benzyl 3,4-dibenzyloxy phenylacetate (16.0 g).

M.p. 71.5°-72.5° C.

Elemental analysis for $C_{29}H_{26}O_4$: Calcd. C: 79.43; H: 5.98. Found C: 79.42; H: 5.86.

ii) Potassium hydroxide (6.2 g) was added to a solution of benzyl 3,4-dibenzyloxyphenylacetate (16.0 g) in methanol (200 ml), followed by stirring at room temperature for 6 hours. The reaction mixture was adjusted to pH 4.0 with 5N hydrochloric acid solution. The solvent was distilled off and to the residue was added water. The precipitated crystal was collected by filtration, washed with water and dried to obtain as colorless crystal 3,4-dibenzyloxyphenylacetic acid (10.0 g).

M.p. 112°-113° C. Elemental analysis for $C_{22}H_{20}O_4$: Calcd. C: 75.84; H: 5.79. Found C: 75.79; H: 5.80.

REFERENCE EXAMPLE 5

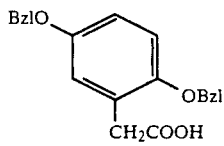

2,5-Dibenzyloxyphenylacetic acid i) In the same manner as in Reference example 4-i), benzyl 2,5-dibenzyloxyphenylacetate was obtained from 2,5-dihydroxyphenylacetic acid.

M.p. 73°-74.5° C.

Elemental analysis for $C_{29}H_{26}O_4$: Calcd. C: 79.43; H: 5.98. Found C: 79.50; H: 5.77.

ii) In the same manner as in Reference example 4-ii), benzyl 2,5-dibenzyloxyphenylacetate was hydrolized to obtain 2,5-dibenzyloxyphenylacetic acid.

M.p. 95.5°-100° C.

Elemental analysis for $C_{22}H_{20}O_4$: Calcd. C: 75.84; H: 5.79. Found C: 75.81; H: 5.63.

What we claim is:

1. A compound of the formula

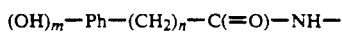

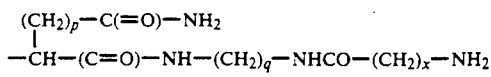

wherein
 m is an integer of 1 to 3;
 n is an integer of 1 or 2;
 p is an integer of 1 or 2;
 q is an integer of 1 to 6;
 x is an integer of 2 to 6;
 Ph is phenylene
or a pharmaceutically acceptable salt thereof.

2. A compound as claimed in claim 1, wherein m is 1 or 2.

3. A compound as claimed in claim 1, wherein

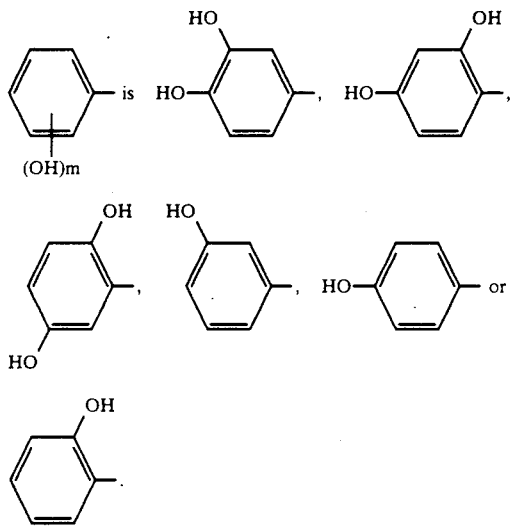

4. A compound as claimed in claim 1, wherein q is 5.

5. A compound of the formula wherein $(OH)_m$—Ph— is hydroxy- or dihydroxy-phenyl and q is as defined in claim 1, or a pharmaceutically acceptable salt thereof.

6. A method for glutamate receptor inhibition which comprises administering to a mammal in need thereof an effective amount of a compound of the formula

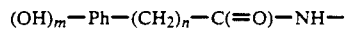

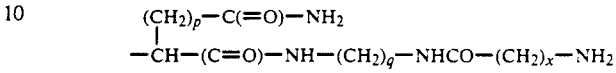

wherein
 m is an integer of 1 to 3;
 n is an integer of 1 or 2;
 p is an integer of 1 or 2;
 q is an integer of 1 to 6;
 x is an integer of 2 to 6;
 Ph is phenylene
or a pharmaceutically acceptable salt thereof.

7. A composition for glutamate receptor inhibition which comprises an effective amount of a compound of the formula

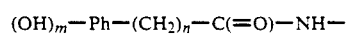

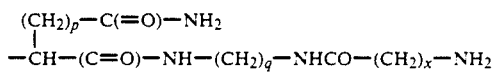

wherein
 m is an integer of 1 to 3;
 n is an integer of 1 or 2;
 p is an integer of 1 or 2;
 q is an integer of 1 to 6;
 x is an integer of 2 to 6;
 Ph is phenylene
or a pharmaceutically acceptable salt thereof, said effective amount being sufficient to provide a glutamate receptor inhibition effect, and a pharmaceutically acceptable carrier, dilient or excipient therefor.

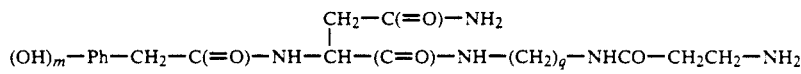

* * * * *